US006987568B2

(12) United States Patent
Dana

(10) Patent No.: US 6,987,568 B2
(45) Date of Patent: Jan. 17, 2006

(54) APPARATUS AND METHOD FOR MEASURING SPATIALLY VARYING BIDIRECTIONAL REFLECTANCE DISTRIBUTION FUNCTION

(75) Inventor: Kristin J. Dana, Staten Island, NY (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 508 days.

(21) Appl. No.: 09/992,486

(22) Filed: Nov. 14, 2001

(65) Prior Publication Data

US 2002/0080357 A1 Jun. 27, 2002

Related U.S. Application Data

(60) Provisional application No. 60/248,814, filed on Nov. 15, 2000.

(51) Int. Cl.
G01N 21/47 (2006.01)
G01B 11/30 (2006.01)

(52) U.S. Cl. ...................... 356/446; 356/600
(58) Field of Classification Search ............... 356/446, 356/600
See application file for complete search history.

(56) References Cited

U.S. PATENT DOCUMENTS

| | | | |
|---|---|---|---|
| 4,285,597 A | 8/1981 | Lamprecht et al. | |
| 4,344,709 A | 8/1982 | Provder et al. | |
| 4,360,275 A | 11/1982 | Louderback | |
| 4,806,018 A | 2/1989 | Falk | |
| 4,815,858 A | 3/1989 | Snail | |
| 4,988,205 A | 1/1991 | Snail | |
| 5,155,558 A | 10/1992 | Tannenbaum et al. | |
| 5,196,906 A | 3/1993 | Stover et al. | |
| 5,241,369 A | 8/1993 | McNeil et al. | |
| 5,270,794 A * | 12/1993 | Tsuji et al. | 356/600 |
| 5,371,582 A * | 12/1994 | Toba et al. | 356/783 |
| 5,541,413 A * | 7/1996 | Pearson et al. | 356/446 |
| 5,636,633 A * | 6/1997 | Messerschmidt et al. | 356/446 |
| 5,637,873 A | 6/1997 | Davis et al. | |
| 5,703,692 A * | 12/1997 | McNeil et al. | 356/446 |
| 5,721,435 A | 2/1998 | Troll | |
| 5,889,593 A | 3/1999 | Bareket | |
| 5,912,741 A | 6/1999 | Carter et al. | |
| 5,926,262 A | 7/1999 | Jung et al. | |
| 5,991,022 A | 11/1999 | Buermann et al. | |
| 6,075,612 A | 6/2000 | Mandella et al. | |
| 6,100,974 A | 8/2000 | Reininger | |

OTHER PUBLICATIONS

Nayar, Shree K. "Catadioptric Omnidirectional Camera." In IEEE Conference on Computer Vision and Pattern Recognition, Puerto Rico: 482-488 (1997).
Ward, Gregory J. "Measuring and Modeling Anisotropic Reflection." Computer Graphics, 26(2): 265-272 (Jul. 1992).

* cited by examiner

Primary Examiner—Richard A. Rosenberger
(74) Attorney, Agent, or Firm—Dann Dorfman Herrell & Skillman; Niels Haun

(57) ABSTRACT

An apparatus and method for measuring spatially varying bidirectional reflectance distribution function and method are provided. The apparatus and method provide means to illuminate different areas of a sample at different angles of incidence and detect the angular variation of radiation emitted from the sample in response to the illumination. The apparatus includes a paraboloidal reflector for delivering the illumination and receiving the radiation emitted by the sample, a radiation source for generating a beam of collimated radiation, a beam steering device for controlling the angle of incidence with which the focused cone of light strikes the sample, and a detector to receive the collected light from the reflector.

110 Claims, 10 Drawing Sheets

APPARATUS AND METHOD FOR MEASURING SPATIALLY VARYING BIDIRECTIONAL REFLECTANCE DISTRIBUTION FUNCTION

RELATED APPLICATIONS

This applications claims the benefit of provisional application Ser. No. 60/248,814, filed on Nov. 15, 2000, the entire contents of which are incorporated herein by reference.

FIELD OF THE INVENTION

The present invention relates generally to a method and apparatus for measuring the distribution of energy emitted by a sample as a function of the angle of emission and the angle of illumination. In particular, the invention relates to a method and apparatus for measuring the spatial variation of the reflectance of a surface in terms of the bidirectional reflectance distribution function.

BACKGROUND OF THE INVENTION

Appearance of real world surfaces is rather complicated, as it varies with the type and direction of illumination as well as with the direction from which it is viewed. Because of this complex variation, measurements of the bidirectional reflectance distribution function (BRDF) are important. The BRDF represents the amount of light reflected from a surface point as a function of four variables (polar and azimuth angles of illumination as well as the polar and azimuth angles of the viewing direction). For many applications, the quantity of interest is light reflection from the entire surface, not just a single surface point. As such, spatially varying BRDF measurements are important as well. For compactness, we refer to a spatially varying BRDF as the bidirectional texture function (BTF).

Capturing surface appearance is important for a large number of applications and industries. In general, any application that uses a computer vision system to recognize and/or classify a surface needs a BRDF/BTF measurement device to support algorithm design, development and testing. Any application that uses computer graphics rendering to synthesize an object's appearance (e.g., on a computer screen) needs a BRDF/BTF measurement device to verify how appearance should be rendered.

In the area of dermatology, a BRDF/BTF measurement device has significant potential. In clinical settings, a BRDF/BTF measurement device can enable remote and/or computer-assisted diagnosis of skin disorders. Quantitative evaluation of the effectiveness of treatments for skin disorders can also be realized with this type of measurement device. In addition, the device can provide quantitative skin appearance assessment to aid in the design, evaluation and marketing of cosmetics.

In industrial settings, measurements of the BRDF/BTF of textiles and coatings can be used for quality control and inventory characterization. Also, measurements of BRDF/BTF of materials can be used in design and planning by enabling accurate rendering prior to manufacturing. Interior design applications can use BRDF/BTF measurements for visualization purposes. This visualization is especially useful for e-commerce solutions that require the consumer to view the appearance of fabrics, wallpaper, wall coatings, etc. under a variety of orientations and illuminations. BRDF/BTF measurements enable a more complete digital representation of any product and therefore are useful in many areas of marketing and advertising. Other applications utilizing BRDF/BTF measurements include watermarking of items for preservation and security and camouflage for the defense industry.

Measurements of the BRDF/BTF are not simple. Most existing technology falls short of the ideal features for such a device. For practicality, the device should be fast and convenient. The apparatus should have as few parts as possible to minimize cost and maximize reliability. The number of moving parts should be minimal, and moving parts should take simple paths.

Measurements of the BRDF are often made using a gonioreflectometer where the illumination and viewing direction are varied over the hemisphere using mechanical means. This brute force method of moving a camera and a light source in all possible 3D directions results in a complex and expensive mechanical device. Such conventional, mechanical devices are difficult to make portable. A portable apparatus is important, because in-field measurements are desirable or necessary for many applications.

Some BRDF measurement methods avoid using a gonioreflectometer by imaging an object that has uniform reflectance and global surface shape so that a varying surface normal of the object leads to multiple reflectance measurements. However the assumption of uniform reflectance is quite restricting and limits the utility of this approach.

Also, measurement of the BRDF at a surface point is not the only item of interest. Instead, devices must have the capability of measuring the BRDF over an extended sample to capture the spatially varying BRDF (BTF). Existing devices for BRDF measurement do not enable convenient, precise control over illumination over a wide range of angles with minimal device components. Another consideration is that the device must be structured so that an extended sample is not re-illuminated by light reflecting from device components. Furthermore, the device must be capable of measuring extended samples that are not globally planar (e.g., measuring the spatially varying BRDF of skin on a human face).

SUMMARY OF THE INVENTION

In accordance with the present invention, an apparatus and method are provided for measuring the bidirectional reflectance distribution function (BRDF) using an optical configuration that yields a compact device, having a small number of moving parts. Furthermore, the present invention permits simplified means of varying the four angles of illumination and detection through simple translation of the optical elements relative to a sample.

A method and apparatus are provided for directing a cone of energy at a prescribed angle of incidence to a location on the surface of a sample and measuring the angular distribution of energy emitted from the sample. The invention is particularly suited to illumination of the sample using electromagnetic radiation and measurement of the bidirectional texture function (BTF).

In general, an apparatus is provided for measuring the energy distribution emitted from a sample as a function of incident beam geometry. A source is provided for producing a substantially collimated source for a radiation beam directed along an optical path. The apparatus includes a paraboloidal reflector having an optical axis oriented parallel to the optical path of the collimated source radiation beam. The paraboloidal reflector is positioned to intercept the collimated radiation beam at a location on the reflector and to focus the intercepted beam to form an incident beam that is directed to strike the sample at a selected sample location with a selected angle of incidence. The radiation from the incident beam is redirected by the sample into an emitted radiation distribution at least a portion of which is intercepted and reflected by the reflector. A detector is provided for receiving the emitted radiation distribution reflected by the reflector. A beam steerer may also be utilized for directing the collimated source radiation beam from the source to a selected location on the reflector. The apparatus may also include a detector translator for moving the detector with respect to the reflector so that varying portions of the emitted radiation distribution are received by the detector.

In a specific embodiment, an apparatus for measuring the bidirectional reflectance distribution function is provided wherein such apparatus comprises a concave, circular paraboloidal reflector having a focal point located at a desired test point on a sample. A light source is provided for generating a beam of collimated radiation which is directed to the reflector along a path parallel to the optical axis of the reflector. Light directed to the reflector parallel to the optical axis of the reflector is focused to the focal point of the reflector regardless of where the light from the light source impinges upon the reflector, and thus, illuminates the sample at a precisely defined test point at the point of focus. The light source may include an aperture to control the diameter of the emitted beam, which is used to define the cone angle of the beam with which the sample is illuminated. The apparatus may further include a beam steering device, such as a movable aperture, for controlling the location at which the collimated beam strikes the reflector thereby controlling the angle of incidence with which the focused cone of light strikes the test point. A translator may also be provided for translating the sample relative to the reflector so that different test points may be addressed on the sample. The translator may move either the sample or the reflector.

The reflector collects light emitted by the sample from the test point and directs the collected light along the optical axis of the reflector. A detector is provided to receive the collected light from the reflector. The location of the detector determines the location at which the emitted light from the sample strikes the reflector, from which the angle at which the light is emitted from the sample surface is calculated. The detector may further include an aperture for defining the diameter of the beam of light received by the detector. The diameter of the light beam received by the detector defines the vertex angle of the cone of light emitted from the sample that is received by the detector. The detector may be moved with respect to the reflector so that the detector receives light from different portions of the reflector, which corresponds to light emitted from the sample at differing angles. For this purpose, a detector translator may be provided to move the detector with respect to the reflector, to detect light emitting from the sample at differing angles. The detector may also include an array of light detecting elements for sampling different portions of the beam reflected from the reflector corresponding to light emitted from the sample at differing angles.

Thus, the apparatus of the present invention provides means to illuminate different areas of the sample at different angles of incidence and to detect the angular variation of radiation emitted from the sample in response to the illumination. The apparatus of the invention is well suited for use as a portable device.

In accordance with the present invention, a method is also provided for measuring the energy distribution emitted from a sample as a function of incident beam geometry. The method includes directing a beam of substantially collimated radiation along an optical path. Next, the method includes receiving the collimated radiation beam by a paraboloidal reflector having an optical axis disposed parallel to the optical path of the collimated radiation. Next, the method includes focusing the received collimated radiation beam to form an incident beam for striking the sample at a selected sample location at a selected angle of incidence so that the radiation from the incident beam is redirected by the sample into an emitted radiation distribution. In a further step, at least a portion of the emitted radiation distribution is intercepted by a reflector and re-directed as an emitted radiation beam. The method also comprises detecting the emitted radiation beam so that a measurement can be made of the intensity of the emitted radiation beam as a function of the angle of emission of the emitted radiation beam and as a functional of the angle of incidence of the incident beam.

BRIEF DESCRIPTION OF THE DRAWINGS

The foregoing summary and the following detailed description of the preferred embodiments of the present invention will be best understood when read in conjunction with the appended drawings, in which.

DETAILED DESCRIPTION OF THE INVENTION

Figure 1:
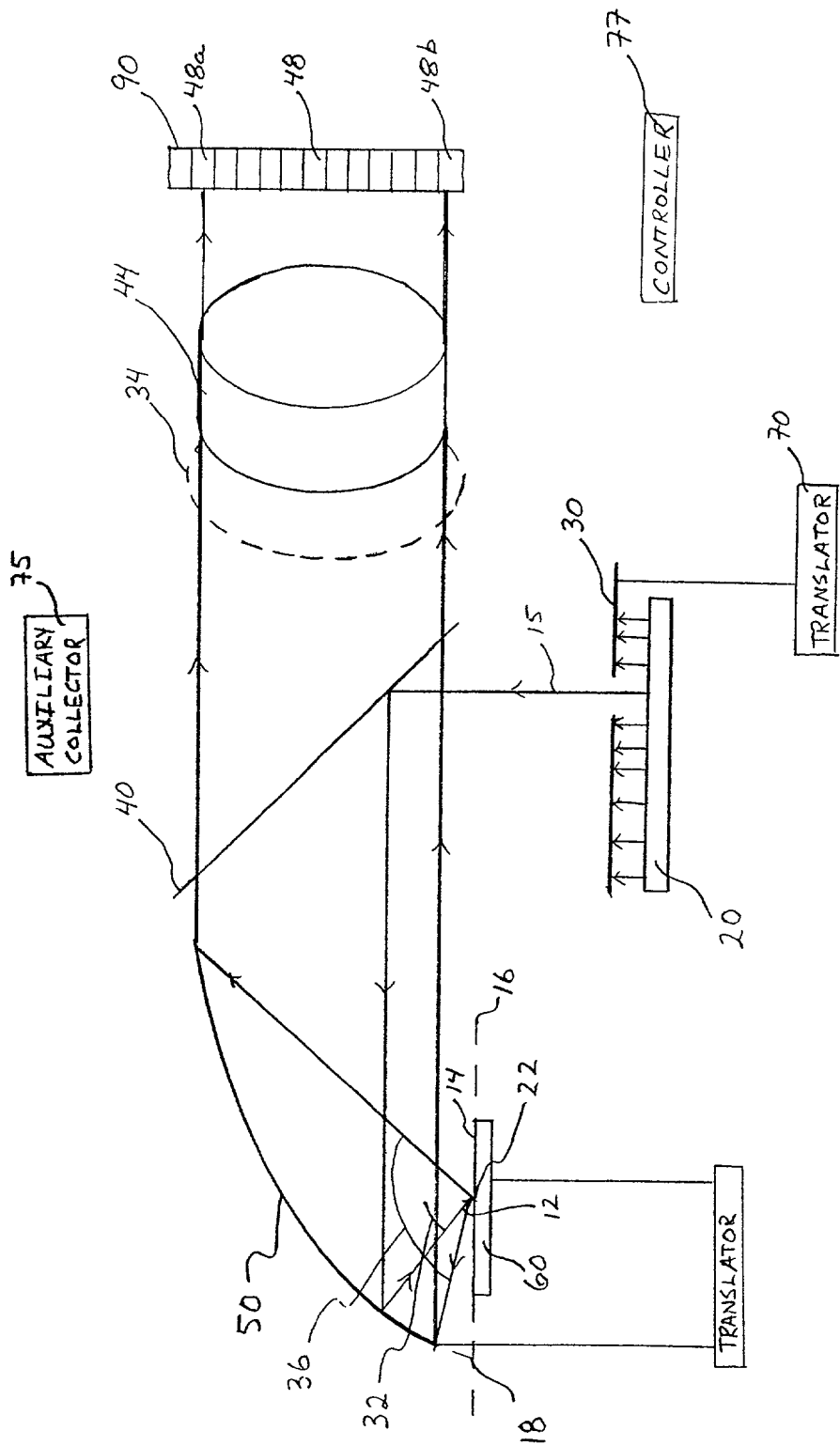
FIG. 1 schematically illustrates a first configuration of the apparatus of the present invention comprising a detector for collecting the full field of emitted radiation.
Figure 2:
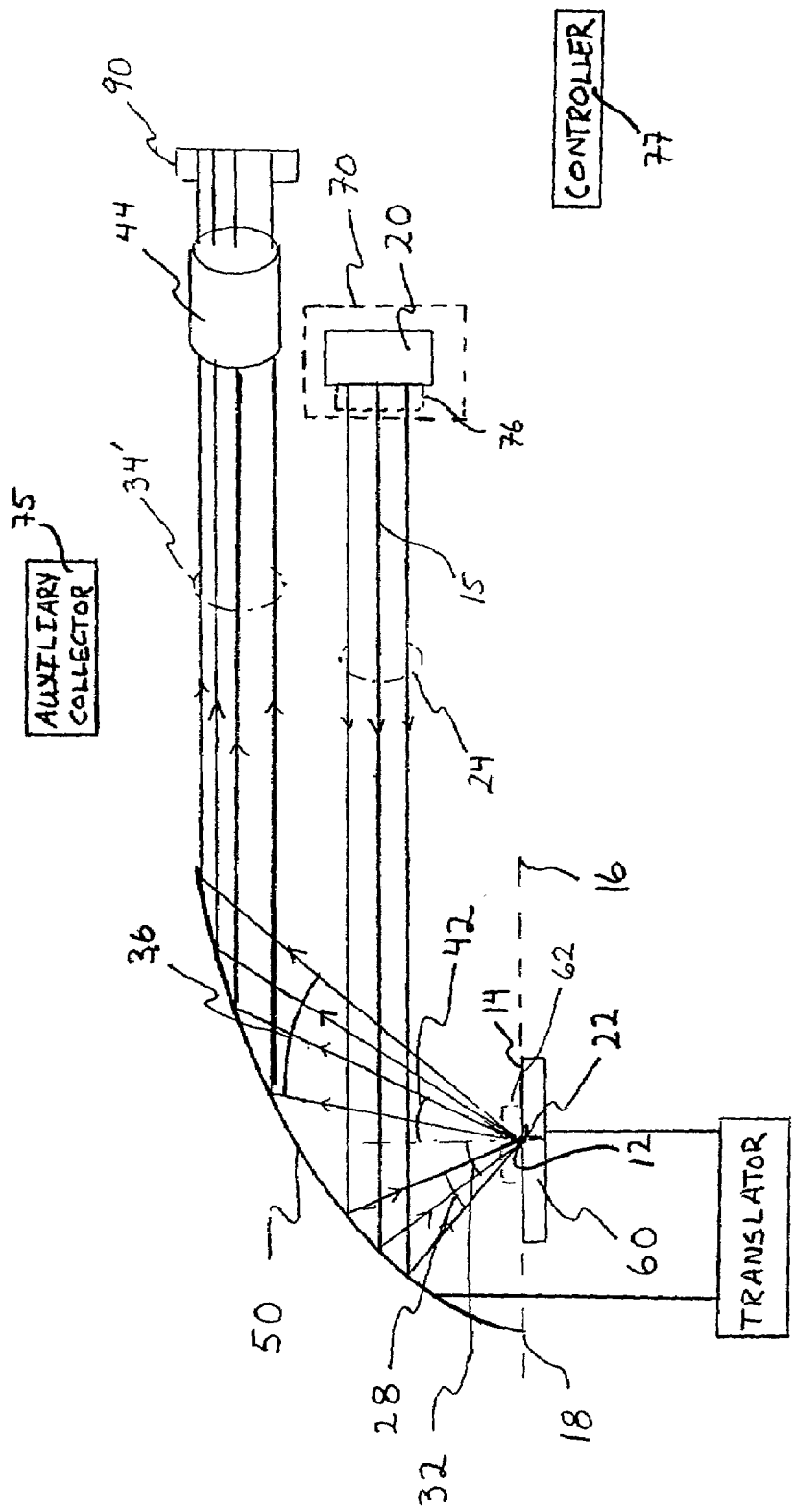
FIG. 2 schematically illustrates a second configuration of the apparatus of the present invention including an apertured detector.
Figure 3:
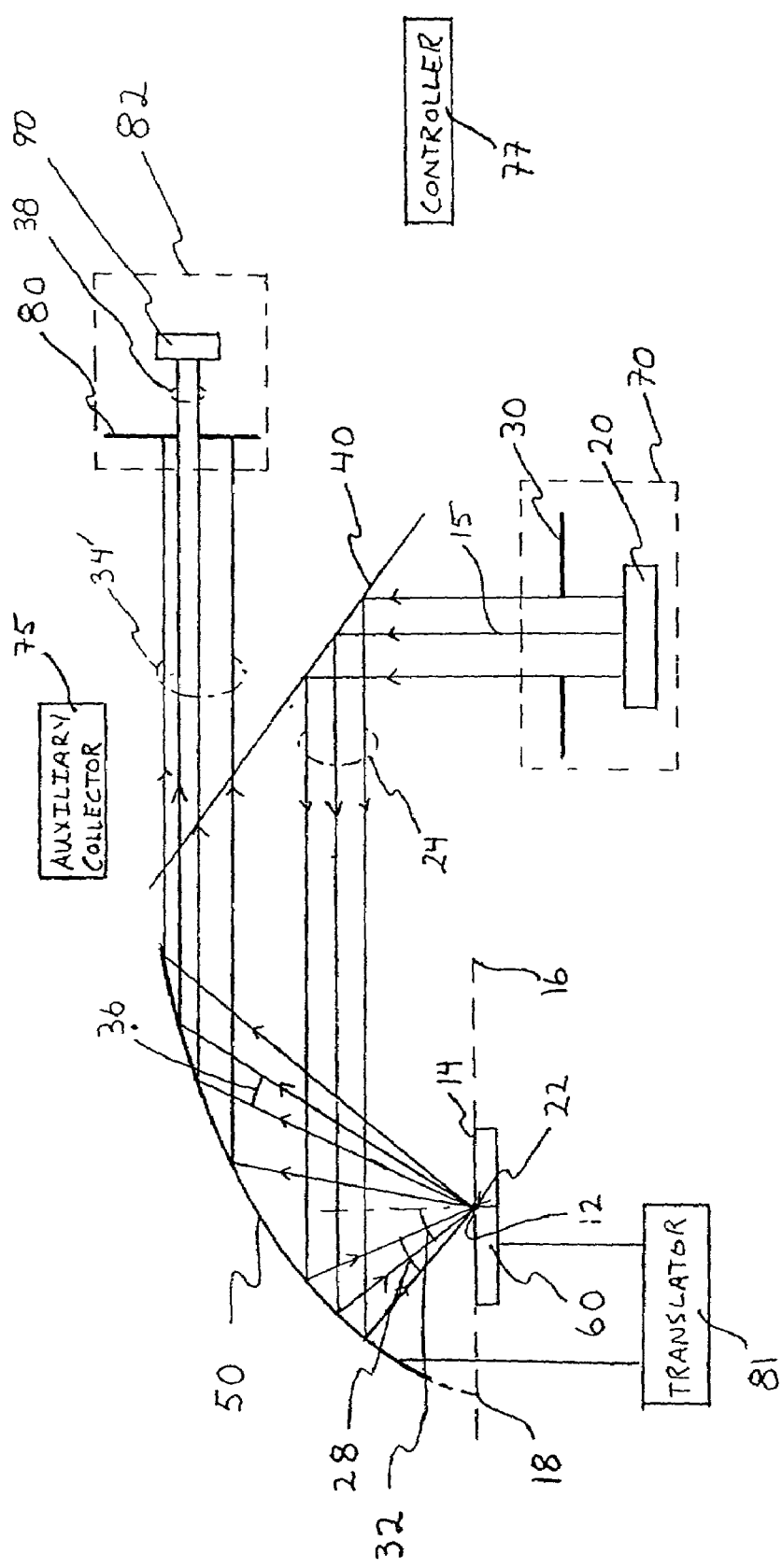
FIG. 3 schematically illustrates a third configuration of the apparatus of the present invention including a source aperture, a detector aperture, and a beam splitter.

Referring now to the drawings, wherein like numerals indicate like elements, there are shown in FIGS. 1–3 illustrations of an apparatus for measuring the energy distribution emitted from a sample as a function of incident beam geometry. The apparatus comprises a concave paraboloidal reflector 50 for both delivering radiation to a test point 12 on the surface 14 of the sample 60 and for collecting radiation emitted by the sample 60. The paraboloidal reflector 50 has an optical axis 16 defined as the line which passes through the vertex 18 of the paraboloid at normal incidence to the surface of the paraboloid. The reflector may be a segment of the paraboloid which does not include the vertex, i.e., an off-axis paraboloidal reflector, as illustrated in FIG. 1. The optical axis 16, as shown in FIGS. 1–3, is parallel to the sample surface 14. In general, however, the optical axis 16 need not be oriented parallel to the sample surface 14.

Generally, the paraboloidal reflector 50 may be a segment of a paraboloid having an elliptical cross-section in a plane perpendicular to the optical axis. For illustration purposes, the paraboloidal reflectors depicted herein are portions of a circular paraboloid, whose cross-section in a plane perpendicular to the optical axis is a circle. Circular paraboloidal reflectors have the property that rays of radiation parallel to the optical axis received by the reflector are focused to a single focal point 22. Accordingly, the focal point 22 of the reflector 50 is located on the surface 14 of the sample 60 to provide the test point 12.

The apparatus further includes a radiation source 20 for illuminating the sample 60. The radiation source 20 produces a collimated beam 24 of radiation having an optical path aligned parallel to the optical axis 16 of the reflector 50. For illustration purposes, all rays of the radiation beams depicted in the accompanying figures are contained within the plane of the drawing. The radiation source 20 may produce acoustic or electromagnetic radiation. For the illustrations that follow, the apparatus and method of the invention are described with respect to electromagnetic radiation without loss of generality.

The electromagnetic radiation produced by the radiation source 20 may include ultraviolet, infrared, and visible wavelengths of radiation. Examples of such sources include a laser, incandescent lamp, fluorescent lamp, infrared source, halogen lamp, and other sources known to those skilled in the art. The source 20 may produce collimated radiation inherently, as by a laser, or the source 20 may include collimating optics to collimate the beam.

The source 20 is positioned with respect to the reflector 50 so that the collimated beam 24 strikes the surface of the reflector 50. Since the beam 24 is collimated and parallel to the optical axis 16 of the reflector 50, all the radiation from the collimated beam 24 incident on the reflector 50 is focused to the focal point 22 of the reflector 50.

Referring to FIGS. 2 and 3, the diameter of the collimated beam 24 incident on the reflector 50 defines the vertex angle 28 of the focused beam, i.e. the angle of the cone delivered to the test point 12. The smaller the diameter of the collimated beam 24, the more acute the vertex angle 28 of the focused beam will be. The diameter of the collimated beam 24 may be controlled by the use of a source aperture 30 as depicted in FIG. 3. The diameter of the source aperture 30 defines the diameter of the collimated beam 24 and thus the vertex angle 28 of the focused beam. The vertex angle 28 may be varied through the use of a variable diameter source aperture. A variable diameter source aperture 30 may include a mechanical iris or liquid crystal shutter having pixels which may be turned on or off to alter the source aperture diameter. Further, the source aperture may include a central obscuration.

The angle of incidence 32 with which the focused beam strikes the sample surface 14, defined as the angle between the central ray 15 of the focused beam and the normal to the sample surface 14, is dictated by the location at which the collimated beam 24 strikes the reflector 50. Accordingly, a beam steerer 70 is provided to control the location at which the collimated beam 24 strikes the reflector 50. For example, the beam steerer 70 may be a translation stage to provide translation of the source 20 with respect to the reflector 50. For configurations which include a source aperture, the translation stage may move the source aperture 30 with or without the source 20 to alter the location on the reflector 50 at which the collimated beam 24 strikes. In particular, as shown in FIG. 1, the beam steerer 70 may be a translator for moving the source aperture 30 to determine the location at which the central ray 15 strikes the reflector 70. Translation of the central ray 15 of the collimated beam 24 and variation of the collimated beam diameter permit the angle of incidence 32 and vertex angle 28 to be controlled.

Alternatively, the beam steerer 70 may comprise one or more rotating aperture disks which transmit radiation from the source 20 to selected portions of the reflector 50, thereby permitting the surface of the reflector 50 to be addressed through the rotating action of the aperture disks. Such a configuration may be particularly desirable to effect rapid addressing of the reflector 50. By coordinating the timing of the rotations of each disk with the frame rate of the video camera, measurements can be conveniently made in real time.

Figure 9A:
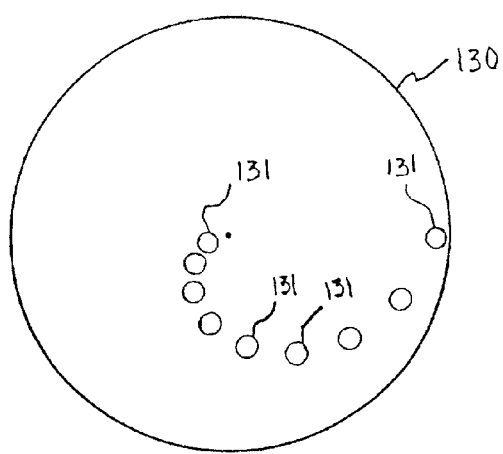
FIG. 9A schematically illustrates a rotatable multi-aperture disk.
Figure 9B:
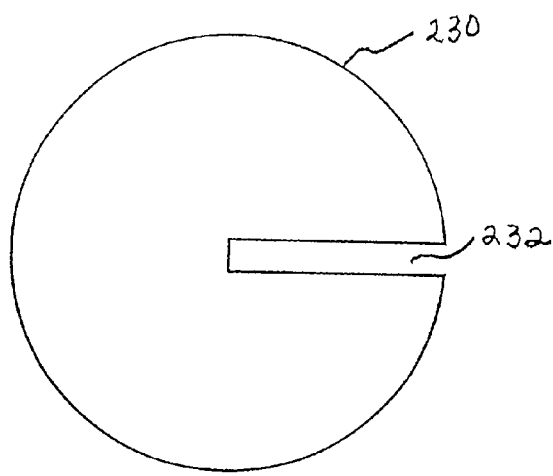
FIG. 9B schematically illustrates a rotatable slit-aperture disk.
Figure 10A:
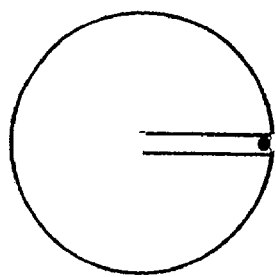
FIG. 10 schematically illustrates elevational views of a rotational beam steerer comprising the slit-aperture disk of FIG. 9B disposed in registration with the multi-aperture disk of FIG. 9A, where the individual FIGS. 10A, B, C, and D illustrate the beam steerer for different degrees of rotation of the multi-aperture disk.
Figure 10B:
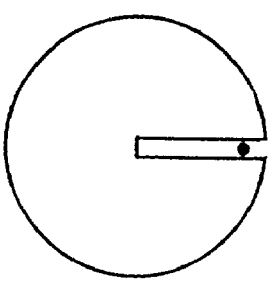
Figure 10C:
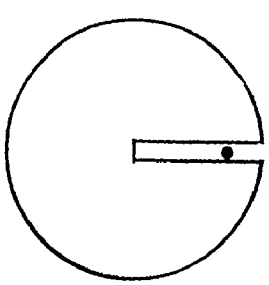
Figure 10D:
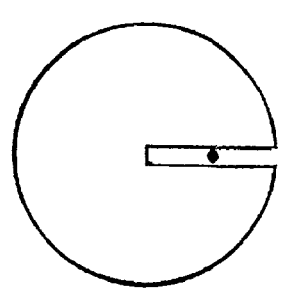
Figure 11A:
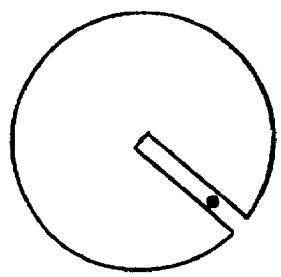
FIGS. 11A–D schematically illustrate the rotational beam steerer of FIGS. 10A–D with the slit-aperture disk at a different angle of rotation than that depicted in FIG. 10.
Figure 11B:
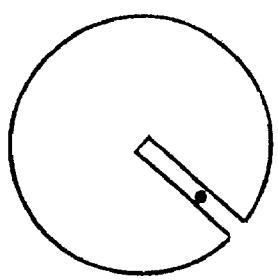
Figure 11C:
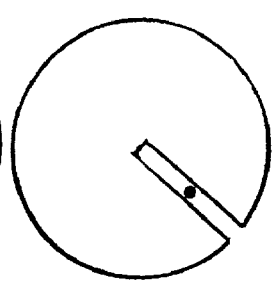
Figure 11D:
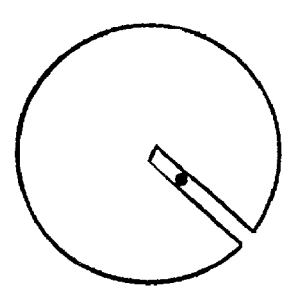

For example, the beam steerer 70 may comprise a multi-aperture disk 130, such as that shown in FIG. 9A, and a slit-aperture disk 230, such as that shown in FIG. 9B. The multi-aperture disk 130 may contain one or more apertures 131 disposed at preselected locations on the multi-aperture disk 130. The locations of the apertures 131 on the multi-aperture disk 130 are selected so that cooperation between the multi-aperture disk 130 and the slit-aperture disk 230 allows selection of a particular aperture 131. For example, the multi-aperture disk 130 may comprise apertures 131 disposed along a spiral pattern, and the slit-aperture disk 230 may comprise a slit 232 which extends along a radius of the slit-aperture disk 230. The slit-aperture disk 230 is disposed in registration with the multi-aperture disk 130 along a common axis of rotation with the optical axis 16, so that the rotation of the multi-aperture disk 130 relative to the slit-aperture disk 230 effects selection of a particular aperture 131 of the multi-aperture disk 130, as shown in FIGS. 10A–D. For a fixed location of the slit-aperture disk 230, rotation of the multi-aperture disk 130 effects addressing of the reflector 50 along a particular radial direction. The orientation of the slit 232 of the slit-aperture disk 230 defines the particular radial direction along which the reflector 50 is addressed. In particular, the angular orientation of the slit 232 of the slit-aperture disk 230 about the optical axis 16 defines the orientation of the radial direction along which the radiation is directed by the rotation as the multi-aperture disk 130 rotates, as shown in FIGS. 11A–D.

The apparatus may further include a sample translator 81 for positioning the sample 60 with respect to the reflector 50. The sample translator 81 may translate the sample 60 and/or the reflector 50 relative to one another. For example, as shown in FIG. 2, the reflector 50 or the sample may be moved along an axis parallel to the optical axis 16. A focusing aperture 62, such as shown in FIG. 2, may be located proximate to the focal point 22 to prevent illumination of areas outside of the focal point 22, which may be caused by imperfections in the surface of the reflector 50 or a lack of collimation of the beam 24, for example.

A second function of the paraboloidal reflector 50 is to collect radiation emitted, such as by reflection or scattering, from the sample 60 and direct the collected radiation to a detector 90. Since the emitted radiation emanates from the location of the focal point 22, the emitted radiation collected by the reflector 50 is reflected as a collimated beam of emitted radiation 34 disposed parallel to the optical axis 16. This feature, along with the arrangement and design of detector 90, enables measurement of the emitted radiation, such as measurement of the bidirectional reflectance distribution function.

As depicted in FIGS. 1–3, the detector 90 is disposed in known location with respect to the reflector 50 to receive the beam of emitted radiation 34 reflected by the reflector 50. In a first detector configuration as shown in FIG. 2, the clear aperture of the detector 90 defines the diameter of the detected radiation beam 34 received by the detector 90. Alternately, in a second detector configuration as shown in FIG. 3, the diameter of the detected radiation beam 38 received by the detector 90 is defined by a detector aperture 80. The diameter of the detected radiation beam 38 received by the detector 90 defines a corresponding cone of detected, emitted radiation 36. The narrower the diameter of the detected radiation beam 38, the narrower the corresponding cone of detected, emitted radiation 36 received by the detector 90. Thus, a narrower beam diameter at detector 90 results in higher angular resolution of measurements of the emitted radiation. The detector aperture 80 for the apparatus shown in FIG. 3 may include a variable aperture for controlling the diameter of the beam received by the detector 90, and thus the angular resolution of the measurement.

The angle of emission 42 of the detected radiation beam 34 or 38 is determined by the location of the detector 90 with respect to the reflector 50. The angle of emission 42 is defined as the angle between the central ray of the cone of detected, emitted radiation 36 and the normal to the sample surface 14. The detector 90 and/or detector aperture 80 may be moved relative to the reflector 50 by use of a detector positioner 82, such as a translation stage. For example, the detector 90 or the detector aperture 80 may be moved transverse relative to the optical axis 16. The angle of emission 42 of the detected radiation beam 34 or 38 is defined as the angle between the central ray of the beam and the normal to the sample surface 14. Knowledge of the location of the detector 90 with respect to the reflector 50 is used to determine the location at which the detected radiation beam 38 struck the reflector 50. From this information, the trajectory of the detected radiation beam 34 or 38 from the location of emission, focal point 22, to the reflector 50 is calculated to establish the angle of emission 42 of the detected radiation beam 34 or 38. Alternatively, the knowledge of the location at which the detected radiation beam 34 struck the reflector 50, along with knowledge of the shape of the reflector 50 at that location, permits the calculation of the trajectory with which the ray struck the reflector 50 based on the laws of reflection. Since the rays depicted in FIGS. 1–3 are contained within the drawing plane, a single angle of emission 42, the azimuthal angle, defines the trajectory for these illustrations. More generally, however, knowledge of the location of the detector 90 with respect to the reflector 50 is used to determine both a polar and azimuth angles of emission.

The detector 90 may comprise a single radiation detecting element, so long as the diameter of the radiation detecting element is smaller than the diameter of the detected radiation beam. If the diameter of the detected radiation beam 34 or 38 is smaller than the diameter of the radiation detecting element, a range of detector positions exist at which the detector 90 may receive the detected radiation beam 34 or 38. As such, there is not a one-to-one correspondence between the detector location and the location on the reflector 50 at which the detected radiation beam 34 or 38 struck the reflector 50. Therefore, the angle of emission 42 is not precisely determined. Accordingly, it is desirable in a system having a single radiation detecting element to have the detecting element be smaller than the detected radiation beam 38. This may be assured by choosing a radiation detecting element with a diameter smaller than the diameter of the collimated beam 24 delivered to the reflector 50. Alternatively, the detector 90 may include multiple radiation detecting elements. For example, a quad detector may be used to determine the location of the centroid of the detected radiation beam 38 having a diameter less than that of the detector 90.

A third configuration of the detector 90, as shown in FIG. 1, includes multiple radiation detecting elements 48 as found in imaging devices, such as a focal plane array or charge coupled device (CCD) camera. Such a configuration provides the distinct benefit of simultaneous measurement of the multiple angles of emission of the detected beam 34. Simultaneous measurement is possible, because each radiation detecting element 48 receives a respective portion of the detected radiation beam 34. The angle of emission of each received portion is determined from the location of the respective radiation detecting element, e.g. elements 48a and 48b, relative to the reflector 50. The size of each radiation detecting element 48 defines an associated cone angle of emitted radiation from the focal point 22 as measured by that element. Thus, the smaller the area of the radiation detecting element 48, the higher the angular resolution of the associated measurement. In the configuration of FIG. 1, additional test points 12 on the sample 60 may be selected by movement of the reflector 50 relative to the sample 60. The detector 90 may be configured to have a field of view sufficiently large to encompass the full range of movement of the reflector 50, so that the detector 90 need not be moved.

Figure 4:
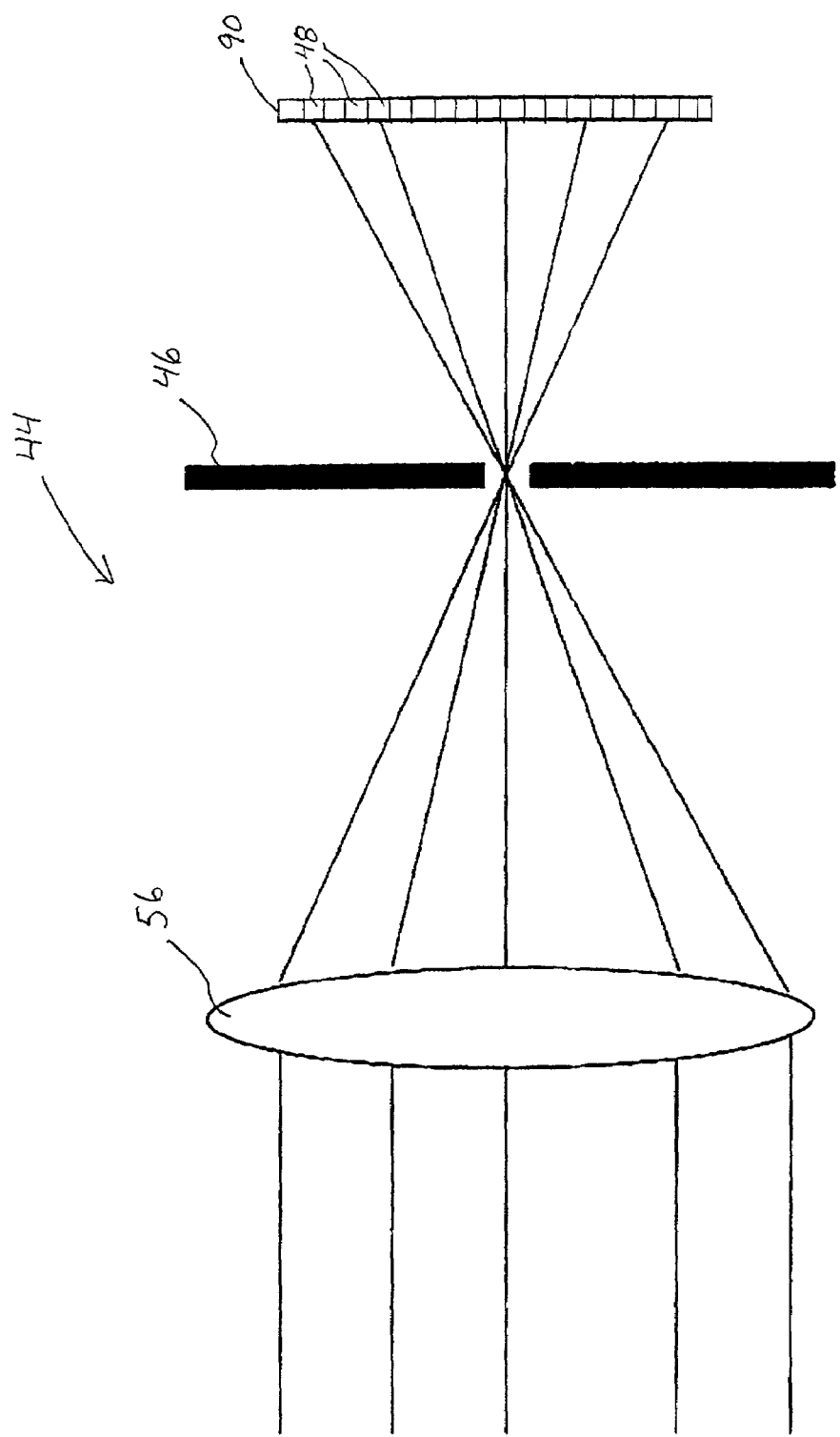
FIG. 4 schematically illustrates a detection device of the invention which includes an orthographic lens to decrease the detection of stray, non-collimated radiation.

The detector 90 may also include an optical system 44, as shown in FIGS. 1 and 2, to direct the emitted beam of radiation 38 to the radiation detecting element of the detector 90. For example, the optical system 44 may include an orthographic lens 56 as depicted in FIG. 4. An auxiliary aperture 46 is located at the focal point of the orthographic lens 56 to prevent non-collimated radiation from reaching the radiation detecting elements 48. The optical system 44 may also include non-imaging optics, such as a compound parabolic concentrator, to collect radiation from the detected beam of radiation 38 and deliver it to the radiation detecting element.

Figure 5:
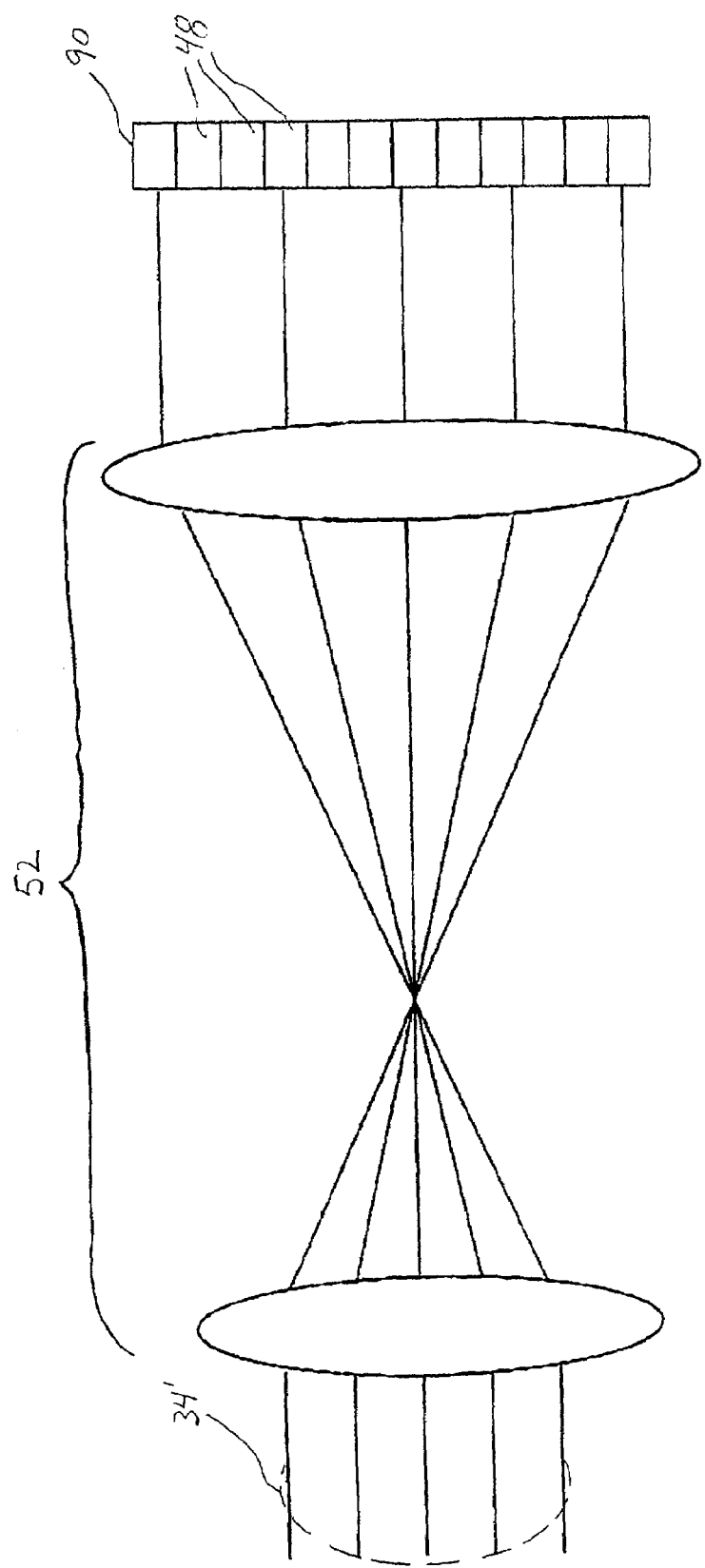
FIG. 5 schematically illustrates a detection device of the present invention which includes a beam expander to increase the measurement resolution.

Still further, the optical system 44 may include a beam expander 52, as shown in FIG. 5, which, when used in conjunction with an multi-element detector such as a CCD, can increase the angular resolution of the detector 90. The beam expander 52 magnifies the diameter of the detected beam of radiation 38 received by the radiation detecting elements 48. Thus, a given portion of the detected beam of radiation 38 is expanded to cover a greater number of the radiation detecting elements 48. This has the effect of increasing the resolution at the cost of decreasing the radiation intensity delivered to the radiation detecting elements 48. Alternatively, the beam expander may be used in reverse configuration as a beam concentrator for increasing the radiation intensity delivered to the radiation detecting elements at the cost of angular resolution.

Figure 6A:
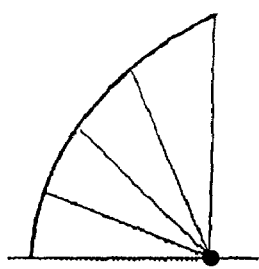
FIGS. 6A and 6B schematically illustrate reflectors of differing longitudinal extent.
Figure 6B:
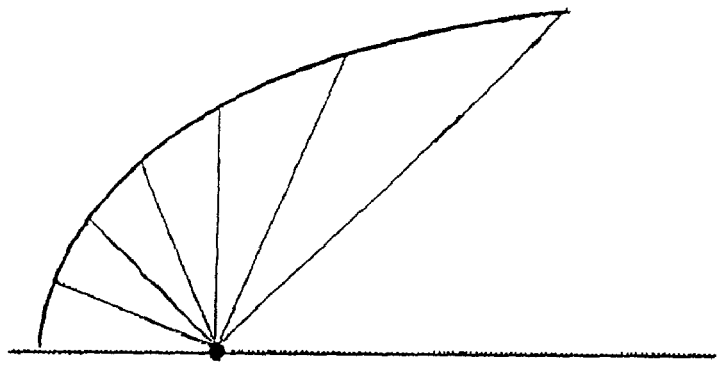

In addition, the apparatus may include an auxiliary collection system 75 to receive radiation emitted from the sample 60 that is not intercepted by the reflector 50 and to direct that radiation to the detector 90. In this manner, the detector 90 receives both the emitted radiation intercepted by the reflector 50 and radiation emitted beyond the collection range of the reflector 50. In addition, reflector 50 may be extended along the optical axis, as shown in FIGS. 6A and 6B, so that a greater range of angles of incidence and angles of emission may be included. The termination point of the reflector 50 as shown is arbitrary.

A reverse beam expander 76 may also be used as part of a source optical system for directing radiation emitted from the source 20 to the reflector 50. For example, a reverse beam expander 76 may be used to concentrate the radiation delivered to the reflector 50 by narrowing the diameter of the collimated beam 24. The source aperture 30 may be used at the input or output of the reverse beam expander to further control the diameter of the collimated beam 24.

The apparatus may include a controller 77 for controlling the source 20, beam steerer 70, the variable source aperture 30, the variable detector aperture 80, the sample translator 81, the detector 90, and/or detector positioner 82. The controller may further perform the calculations necessary to determine detected radiation intensity as a function of angle emission from the sample and the angle of incidence of the illumination of the sample.

The apparatus may also include a beam splitter 40, as depicted in FIGS. 1 and 3, disposed between the source 20 and the reflector 50. The beam splitter 40 permits the source 20 to be located away from the detector 90 so that the source 20 does not block emitted radiation reflected by the reflector 50 from reaching the detector 90. The beam splitter 40 is disposed to receive radiation emitted by the radiation source 20 and to redirect the radiation to the reflector 50. The beam splitter 40 is further designed to transmit at least a portion of the beam of emitted radiation 34. Further variations in the configuration of the apparatus can be made to permit specialized measurements of differing types of samples.

The apparatus is suited to testing samples that emit radiation by reflection, scattering, diffraction, or stimulated emission, such as fluorescence. The radiation may be emitted from the surface of the sample or from the volume of the sample. For example, the focal point may be located within the volume of the sample rather than on the surface of the sample so that the test point is disposed within the sample. Such a configuration could be particularly useful in testing a material for internal scattering sites or for exciting fluorescence within the material.

For example, one application may be the detection of defects that scatter the incident radiation. These types of defects may be located on the surface of a sample or within the volume of the sample. In such an application, the beam may be delivered to the sample in the same manner as described above. However, it may be advantageous to increase the signal-to-noise ratio by blocking the specularly reflected beam from reaching the detector to enhance detection of weakly scattering defects. For this purpose, the detector aperture 80 may include a central obscuration to block the specularly reflected component of the beam of emitted radiation 34. The location of the specularly reflected beam in the detection plane is calculated from the known location of the source 20 with respect to the reflector 50 using standard ray-tracing techniques. From this data, the central obscuration of the detector aperture may be placed in the proper location to block the specularly reflected component of the beam of emitted radiation 34. Devices such as a liquid crystal shutter whose pixels may be turned on and off to alter the shape of the aperture and the size and location of the central obscuration may be particularly useful in this configuration.

Alternatively, the specularly reflected component of the beam of emitted radiation 34 may be prevented from reaching the detector 90 through the use of one or more polarizers. In this type of configuration, an inherently linearly polarized source, e.g. a laser, may be used as the source 20 or a linear polarizer may be placed within the collimated beam 24 to create a linearly polarized collimated beam 24. A crossed linear polarizer is placed in the emitted beam of radiation 38, between the reflector 50 and the detector 90, to extinguish the specularly reflected component while transmitting the diffusely reflected or scattered components to the detector 90. This type of configuration is effective where the specularly reflected beam retains its linear polarization state and the diffusely reflected or scattered beam includes a component of radiation that does not retain the linear polarization state.

Another application benefitting from a specialized configuration of the apparatus is the detection of stimulated emissions of radiation. In this type of application, the source 20 is designed to emit radiation having a spectral component suited to create fluorescence in the sample. For example, the source 20 may include a laser or may include a spectral filter to limit the spectral output of the source 20 to those components that excite fluorescence in the sample. To increase the signal-to-noise ratio of detected emitted radiation, the detector 90 may include a complementary spectral filter which blocks radiation having the same spectral content as that of the source 20. The spectral filter may include a monochrometer or other equivalent device.

In addition to making measurements of BRDF, the apparatus may be designed to measure the color of the sample as a function of the illumination geometry. For these purposes, the detector 90 may include a colorimeter or a spectrophotometer. These devices may be integral to the detector 90 or may be separate devices designed to receive the emitted beam of radiation 34. In some fields, it is desirable to subject a sample to ambient illumination in addition to illumination from the source 20. For this purpose, the reflector 50 may be a half silvered reflector that permits ambient radiation to pass through the reflector and illuminate the surface of the sample. Further, it may be desirable that the apparatus take the form of a hand-held device.

Although the above description and accompanying figures describe the use of a circular paraboloidal reflector, an elliptical paraboloidal reflector could also be used. For example, an elliptical paraboloidal reflector could be particularly useful in delivering radiation to differing test points of the sample without the need to translate the source 20, reflector 50, or sample 60. The multiple "focal points" of the elliptical paraboloidal reflector may be employed to address the different test points on the sample 60.

The radiation source 20 could be adapted to produce a collimated, planar beam of radiation where the planar beam is contained in an axial plane that contains the optical axis 16. This configuration of the source 20 utilizes the feature of elliptical paraboloidal reflectors whereby rays of radiation parallel to the optical axis and contained within an axial plane are focused to a point. The beam steerer 70 could be configured to rotate the collimated, planar beam of radiation about the optical axis 16, thus causing the beam of radiation to strike the elliptical paraboloidal reflector at differing axial plane cross-sections. Differing axial plane cross-sections of an elliptical paraboloidal reflector contain parabolic cross-sections of different shape, each parabolic cross-section having a different focal point. Thus, as the collimated, axial planar beam of radiation is rotated about the optical axis 16, the beam intersects the elliptical paraboloidal reflector at different parabolic cross-sections, and is therefore focused to different focal points/test points of the sample 60. The range of test points that may be addressed by this method is limited to a region corresponding to the locus of focal points defined by the shape of the elliptical paraboloidal reflector. The more eccentric the elliptical cross-section of the elliptical paraboloidal reflector, the larger the region of focal points will be. Conversely, for an eccentricity of one, i.e., a circular paraboloidal reflector, the locus of focal points is a single point.

Figure 7:
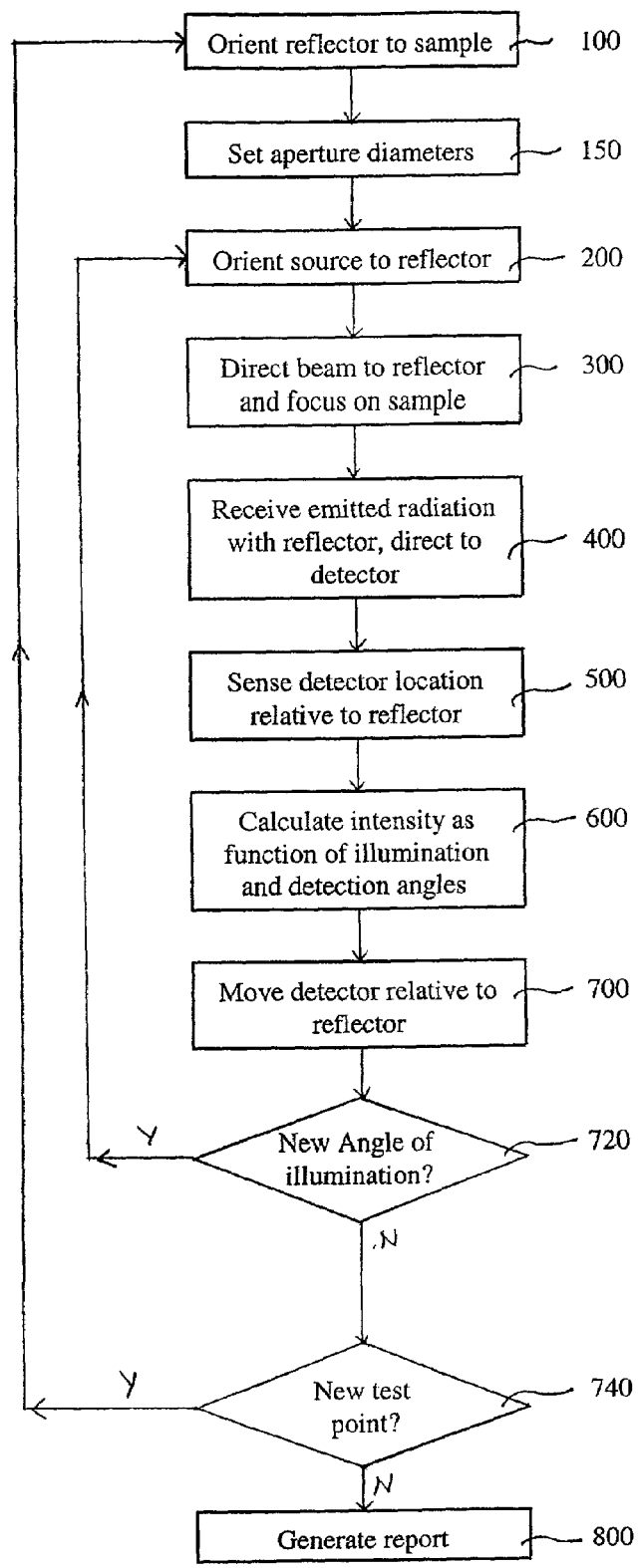
FIG. 7 illustrates a flowchart representing steps of operation of a method of the present invention.

A method of use of the apparatus of the present invention can be understood by its application to the measurement of the BRDF. Referring to FIG. 7, measurement begins with orienting the sample relative to the reflector, at step 100, so that the focal point of the reflector is located at the desired test point of the sample. The reflector may be moved vertically to account for variations in the height of the sample, such as for non-planar samples. The vertex angle of the cone of illumination is optionally selected by adjusting the diameter of the variable source aperture at step 150. The vertex angle of the cone of radiation to be received by the detector may also be selected by adjusting the diameter of a variable detector aperture at step 150. The location of the source with respect to the reflector, which is specified by moving the source or the reflector or both with respect to one another, is determined at step 200. If a source aperture is used, the source aperture is moved with respect to the reflector at step 200. Specification of the location of the source/source aperture with respect to the reflector determines the angle of incidence with which the cone of radiation strikes the sample. A collimated beam of radiation is directed from the source to the reflector along the optical axis of the reflector and focused at the test point of the sample at step 300. The sample, in response to the received radiation, emits diffusely reflected radiation which is received at various points on the reflector. The reflector directs the received emitted radiation to the detector along the optical axis of the reflector at step 400. At step 500, the location of the detector with respect to the reflector is sensed and the radiation intensity received by the detector is determined. From this information, the intensity of the received emitted radiation is calculated as a function of the polar and azimuth angles of emission from the sample and the polar and azimuth angles of incidence of the illumination, at step 600. The detector and/or detector aperture, if used, are translated with respect to the reflector at step 700 to receive additional portions of the reflected emitted radiation beam. For each location of the detector at which radiation is detected, the calculations of step 600 are repeated.

Figure 8:
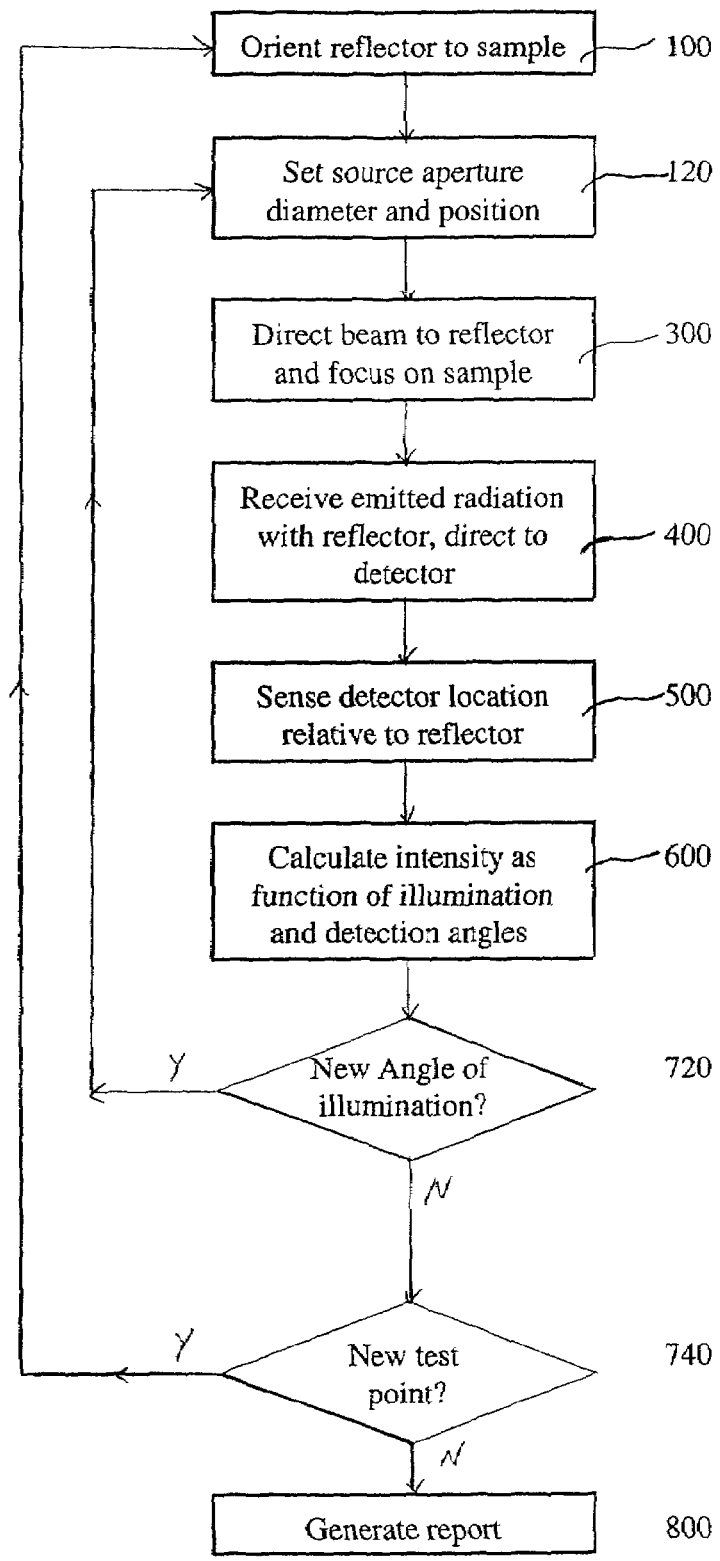
FIG. 8 illustrates a flowchart representing steps of operation of a second method of the present invention.

If measurements for different angles of incidence of illumination are desired, as decided at step 720, steps 200–700 are repeated. If measurements are desired for additional test points of the sample, as decided at step 740, steps 100–720 are repeated. Once all desired measurements are made, a report may be generated, including graphical output, at step 800. Similar procedures may be used in accordance with the above method to operate the specialized configurations of the apparatus described above. For example, the method of FIG. 8 is particularly suited to operation of the configuration of FIG. 1. The steps of FIG. 8 correspond to those of FIG. 7 with the difference that the source aperture in moved relative to the reflector as part of step 120. An additional difference is that the detector need not be moved, so step 700 is absent from FIG. 8.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

I claim:

1. An apparatus for measuring, as a function of incident beam geometry, the energy distribution emitted from a sample comprising:
    a) a source for producing a substantially collimated source radiation beam directed along an optical path;
    b) a paraboloidal reflector, having an optical axis disposed substantially parallel to the tangent of the sample surface at a selected sample location to be measured, the reflector positioned to intercept the collimated radiation beam at a first location on the reflector and to focus the intercepted beam to form an incident beam that strikes the sample at the selected sample location with a selected angle of incidence, whereupon the radiation from the incident beam is redirected by the sample into an emitted radiation distribution at least a portion of which is intercepted and reflected by the reflector;
    c) a detector for receiving the emitted radiation distribution reflected by the reflector; and
    d) a controller for varying the relative orientation of the source to the mirror to vary the angle of incidence of illumination, and for calculating the distribution of radiation received by the detector as a function of angle of emission from the sample and as a function of the angle of incidence of the illumination of the sample to compute a BRDF of the sample.

2. The apparatus according to claim 1 wherein the source comprises a beam steerer for directing the radiation beam to determine the position of the first location on the reflector.

3. The apparatus according to claim 2 wherein the beam steerer comprises a translator for moving the source with respect to the reflector.

4. The apparatus according to claim 1 comprising a source aperture disposed along the optical path between the source and the reflector, the source aperture defining the width of the beam intercepted by the reflector from the source.

5. The apparatus according to claim 4 comprising a translator for moving the source aperture with respect to the reflector whereby the position of the first location is determined.

6. The apparatus according to claim 4 wherein the source aperture comprises a variable aperture.

7. The apparatus according to claim 4 wherein the source aperture comprises a liquid crystal shutter.

8. The apparatus according to claim 4 wherein the source aperture comprises a circular aperture.

9. The apparatus according to claim 1 wherein the source comprises a radiation emitter and a collimator for collimating the radiation emitted by the radiation emitter.

10. The apparatus according to claim 1 wherein the reflector is a circular paraboloid.

11. The apparatus according to claim 1 wherein the reflector is a half-silvered reflector.

12. The apparatus according to claim 1 wherein the optical axis of the reflector is substantially parallel to a plane which contains the surface of the sample.

13. The apparatus according to claim 1 wherein the reflector is a concave paraboloid.

14. The apparatus according to claim 1 wherein the reflector intercepts the entire emitted radiation distribution.

15. The apparatus according to claim 1 wherein the reflector is an off-axis paraboloid.

16. The apparatus according to claim 1 comprising a beam splitter disposed along the optical path between the source and the reflector, for receiving the source radiation beam and directing the source radiation beam to the first location on the reflector.

17. The apparatus according to claim 1 wherein the emitted radiation distribution comprises at least one radiation ray and the detector comprises a detection plane for receiving the radiation ray, wherein the location at which the radiation ray strikes the detection plane corresponds to an angle of incidence with which the radiation ray struck the reflector.

18. The apparatus according to claim 17 wherein the detector comprises an imaging system for directing the radiation ray to the detection plane.

19. The apparatus according to claim 17 wherein the detector comprises an array of radiation detecting elements disposed along the detection plane, wherein the radiation ray strikes a respective radiation detecting element, the respective element associated with the angle of incidence with which the respective radiation ray struck the reflector.

20. The apparatus according to claim 19 wherein the detection array comprises a two-dimensional array of radiation detecting elements.

21. The apparatus according to claim 20 wherein the location of a respective radiation detecting element corresponds to a respective angle of incidence at which a respective ray, received by the respective element, struck the reflector.

22. The apparatus according to claim 21 wherein the detector comprises an imaging system for directing the respective radiation ray to the respective radiation detection plane.

23. The apparatus according to claim 19 wherein the detector comprises a beam expander disposed between the reflector and the radiation detecting element.

24. The apparatus according to claim 1 wherein detector comprises an orthographic lens having an aperture stop disposed proximate to the focal point of the lens.

25. The apparatus according to claim 1 wherein the detector comprises at least one of a linear polarizer, an elliptical polarizer, a circular polarizer, an optical retarder, or spectral filter.

26. The apparatus according to claim 1 wherein the detector comprises a polarizer for blocking a component of the emitted radiation distribution having the same polarization state as that of the source radiation beam.

27. The apparatus according to claim 1 wherein the detector comprises a spectral filter for blocking a component of the emitted radiation distribution within the spectral range of the source radiation beam.

28. The apparatus according to claim 1 wherein the detector comprises a spectral filter for transmitting a component of the emitted radiation distribution within the spectral range of the source radiation beam.

29. The apparatus according to claim 1 comprising a detector translator for moving the detector with respect to the reflector whereby varying portions of the emitted radiation distribution are received by the detector.

30. The apparatus according to claim 29 comprising a detector aperture disposed between the detector and the reflector to intercept the emitted radiation distribution, to pass a portion of the emitted radiation distribution to the detector.

31. The apparatus according to claim 30 wherein the detector translator translates the detector and the detector aperture, the detector and detector aperture disposed in fixed relation to one another.

32. The apparatus according to claim 30 wherein the detector aperture comprises a variable aperture.

33. The apparatus according to claim 30 wherein the detector aperture comprises a liquid crystal shutter.

34. The apparatus according to claim 30 wherein the detector aperture comprises a circular aperture.

35. The apparatus according to claim 30 wherein the detector aperture comprises a central obscuration disposed within the emitted radiation distribution to block a specularly reflected component of the emitted radiation distribution from transmission to the detector.

36. The apparatus according to claim 1 wherein the focal point of the reflector is located proximate to the selected sample location.

37. The apparatus according to claim 36 wherein the focal point is located within the volume of the sample.

38. The apparatus according to claim 36 wherein the focal point is located proximate to the surface of the sample.

39. The apparatus according to claim 1 comprising a sample aperture disposed proximate to the focal point of the reflector.

40. The apparatus according to claim 1 comprising a reflector translator for moving the reflector with respect to the sample.

41. The apparatus according to claim 1 comprising a sample translator for moving the sample with respect to the reflector.

42. The apparatus according to claim 1 wherein the source comprises at least one of a linear polarizer, an elliptical polarizer, a circular polarizer, an optical retarder, or spectral filter.

43. The apparatus according to claim 1 wherein the source emits electromagnetic radiation.

44. The apparatus according to claim 1 wherein the source emits the collimated source radiation in an axial plane which contains the optical axis.

45. The apparatus according to claim 44 wherein the reflector is an elliptical paraboloidal reflector.

46. The apparatus according to claim 1 wherein the detector comprises at least one of a charge coupled device, a focal plane array, colorimeter, or spectrophotometer.

47. An apparatus for measuring, as a function of incident beam geometry, the energy distribution emitted from a sample comprising:
   a) a source for producing a substantially collimated source radiation beam directed along an optical path;
   b) a paraboloidal reflector, having an optical axis disposed substantially parallel to the tangent of the sample surface at a selected sample location to be measured, the reflector positioned to intercept the collimated radiation beam at a first location on the reflector and to focus the intercepted beam to form an incident beam that strikes the sample at the selected sample location with a selected angle of incidence, whereupon the radiation from the incident beam is redirected by the sample into an emitted radiation distribution at least a portion of which is intercepted and reflected by the reflector;
   c) a detector for receiving the emitted radiation distribution reflected by the reflector;

d) a beam steerer for directing the radiation beam to the first location on the reflector;

e) a detector translator for moving the detector with respect to the reflector whereby varying portions of the emitted radiation distribution are received by the detector; and f) a controller for controlling the beam steerer to vary the relative orientation of the source to the mirror to vary the angle of incidence of illumination, and for calculating the distribution of radiation received by the detector as a function of angle of emission from the sample and as a function of the angle of incidence of the illumination of the sample to compute a BRDF of the sample.

48. The apparatus according to claim 47 wherein the beam steerer comprises a translator for moving the source with respect to the reflector.

49. The apparatus according to claim 47 comprising a source aperture disposed along the optical path between the source and the reflector, the source aperture defining the width of the beam intercepted by the reflector from the source.

50. The apparatus according to claim 49 wherein the beam steerer moves the source aperture with respect to the reflector.

51. The apparatus according to claim 50 wherein the source aperture comprises a variable aperture.

52. The apparatus according to claim 51 wherein the source aperture comprises a liquid crystal shutter.

53. The apparatus according to claim 47 wherein the source comprises a radiation emitter and a collimator for collimating the radiation emitted by the radiation emitter.

54. The apparatus according to claim 47 wherein the reflector is a circular paraboloid.

55. The apparatus according to claim 47 wherein the beam steerer comprises a rotatable aperture disk.

56. The apparatus according to claim 47 wherein the optical axis of the reflector is substantially parallel to a plane which contains the surface of the sample.

57. The apparatus according to claim 47 wherein the reflector is a concave paraboloid.

58. The apparatus according to claim 47 wherein the reflector intercepts the entire emitted radiation distribution.

59. The apparatus according to claim 47 wherein the reflector is an off-axis paraboloid.

60. The apparatus according to claim 47 comprising a beam splitter disposed along the optical path between the source and the reflector, for receiving the source radiation beam and directing the source radiation beam to the first location on the reflector.

61. The apparatus according to claim 47 wherein the emitted radiation distribution comprises at least one radiation ray and the detector comprises a detection plane for receiving the radiation ray, wherein the location at which the radiation ray strikes the detection plane corresponds to an angle of emission with which the radiation ray was emitted from the sample.

62. The apparatus according to claim 61 wherein the detector comprises an imaging system for directing the radiation ray to the detection plane.

63. The apparatus according to claim 61 wherein the detector comprises an array of radiation detecting elements disposed along the detection plane, wherein the radiation ray strikes a respective radiation detecting element, the respective element associated with the angle of emission with which the radiation ray was emitted from the sample.

64. The apparatus according to claim 63 wherein the detection array comprises a two-dimensional array of radiation detecting elements.

65. The apparatus according to claim 64 wherein the location of a respective radiation detecting element corresponds to a respective angle of emission with which the radiation ray, received by the respective element, was emitted from the sample.

66. The apparatus according to claim 65 wherein the detector comprises an imaging system for directing the respective radiation ray to the respective radiation detection plane.

67. The apparatus according to claim 63 wherein the detector comprises a beam expander disposed between the reflector and radiation detecting element.

68. The apparatus according to claim 47 wherein detector comprises an orthographic lens having an aperture stop disposed proximate to the focal point of the lens.

69. The apparatus according to claim 47 wherein the detector comprises at least one of a linear polarizer, an elliptical polarizer, a circular polarizer, an optical retarder, or spectral filter.

70. The apparatus according to claim 47 wherein the detector comprises a polarizer for blocking a component of the emitted radiation distribution having the same polarization state as that of the source radiation beam.

71. The apparatus according to claim 47 wherein the detector comprises a spectral filter for blocking a component of the emitted radiation distribution within the spectral range of the source radiation beam.

72. The apparatus according to claim 47 wherein the detector comprises a spectral filter for transmitting a component of the emitted radiation distribution within the spectral range of the source radiation beam.

73. The apparatus according to claim 47 comprising a detector aperture disposed between the detector and the reflector to intercept the emitted radiation distribution, to pass a portion of the emitted radiation distribution to the detector.

74. The apparatus according to claim 73 wherein the detector translator translates the detector and the detector aperture, the detector and detector aperture disposed in fixed relation to one another.

75. The apparatus according to claim 73 wherein the detector aperture comprises a variable aperture.

76. The apparatus according to claim 73 wherein the detector aperture comprises a liquid crystal shutter.

77. The apparatus according to claim 73 wherein the detector aperture comprises a circular aperture.

78. The apparatus according to claim 73 wherein the detector aperture comprises a central obscuration disposed within the emitted radiation distribution to block a specularly reflected component of the emitted radiation distribution from transmission to the detector.

79. The apparatus according to claim 47 wherein the focal point of the reflector is located proximate to the selected sample location.

80. The apparatus according to claim 79 wherein the focal point is located within the volume of the sample.

81. The apparatus according to claim 79 wherein the focal point is located proximate to the surface of the sample.

82. The apparatus according to claim 47 comprising a reflector translator for moving the reflector with respect to the sample.

83. The apparatus according to claim 47 comprising a sample translator for moving the sample with respect to the reflector.

84. The apparatus according to claim 47 wherein the source comprises at least one of a linear polarizer, an elliptical polarizer, a circular polarizer, an optical retarder, or spectral filter.

85. The apparatus according to claim 47 wherein the source emits electromagnetic radiation.

86. The apparatus according to claim 47 wherein the source emits the collimated source radiation in an axial plane that contains the optical axis.

87. The apparatus according to claim 86 wherein the reflector is an elliptical paraboloidal reflector.

88. The apparatus according to claim 47 wherein the detector comprises at least one of a charge coupled device, a focal plane array, colorimeter, or spectrophotometer.

89. A method for measuring, as a function of incident beam geometry, the energy distribution emitted from a sample comprising the steps of:
   a) directing a beam of substantially collimated radiation along an optical path;
   b) receiving the collimated radiation beam by a paraboloidal reflector, having an optical axis disposed substantially parallel to the tangent of the sample surface at a selected sample location to be measured, and focusing the received beam to form an incident beam that strikes the sample at the selected sample location with a selected angle of incidence, whereupon the radiation from the incident beam is redirected by the sample into an emitted radiation distribution;
   c) intercepting, with the reflector, at least a portion of the emitted radiation distribution and directing such portion of the emitted radiation distribution as an emitted radiation beam;
   d) detecting the emitted radiation beam so that a measurement can be made of the intensity of the emitted radiation beam as a function of an angle of emission of the emitted radiation beam and as a function the angle of incidence of the incident beam.

90. The method of claim 89 wherein step of directing the substantially collimated beam comprises the step of directing the collimated radiation beam to the first location on the reflector with a beam steerer to determine the angle of incidence.

91. The method of claim 90 wherein step of directing the substantially collimated beam comprises the step of defining the width of the beam received by the reflector from the source by varying the diameter of a source aperture disposed between the source and the reflector.

92. The method of claim 89 wherein step of directing the substantially collimated beam includes the step of directing the beam to the first location on the reflector using a beam splitter disposed along the optical path between the source and the reflector.

93. The method of claim 89 wherein step of intercepting the emitted radiation distribution includes intercepting the entire emitted radiation distribution with the reflector.

94. The method of claim 89 wherein step of detecting the emitted radiation beam includes the step of determining the angle of emission with which the emitted radiation beam was emitted from the sample.

95. The method of claim 89 wherein step of detecting the emitted radiation beam includes the step of receiving at least one radiation ray of the emitted radiation beam at a detection plane of the detector, and determining, from the location at which the radiation ray strikes the detection plane, the angle of emission with which the detected emitted radiation beam was emitted from the sample.

96. The method of claim 89 wherein step of detecting the emitted radiation beam includes the step of moving the detector with respect to the reflector whereby varying portions of the emitted radiation distribution are received by the detector.

97. The method of claim 96 wherein step of detecting the emitted radiation beam comprises the step of defining the width of the emitted radiation beam detected by the detector by varying the diameter of a detector aperture disposed between the detector and the reflector.

98. The method of claim 97 wherein step of detecting the emitted radiation beam includes the step of moving the detector and detector aperture with respect to the reflector, whereby varying portions of the emitted radiation distribution are received by the detector.

99. The method of claim 89 wherein step of detecting the emitted radiation beam includes the step of blocking a specularly reflected component of the emitted radiation distribution from transmission to the detector using a central obscuration of a detector aperture.

100. The method of claim 89 wherein step of intercepting the emitted radiation distribution includes the step of focusing the incident beam proximate to the selected sample location.

101. The method of claim 89 wherein step of intercepting the emitted radiation distribution includes the step of focusing the incident beam within the volume of the sample.

102. The method of claim 89 wherein step of intercepting the emitted radiation distribution includes the step of focusing the incident beam proximate to the surface of the sample.

103. The method of claim 89 comprising the step of moving the reflector with respect to the sample.

104. An apparatus for measuring, as a function of incident beam geometry, the energy distribution emitted from a sample comprising:
   a) a source for producing a substantially collimated source radiation beam directed along an optical path;
   b) a paraboloidal reflector, having an optical axis disposed substantially parallel to the tangent of the sample surface at a selected sample location to be measured, the reflector positioned to intercept the collimated radiation beam at a first location on the reflector and to focus the intercepted beam to form an incident beam that strikes the sample at the selected sample location with a selected angle of incidence, whereupon the radiation from the incident beam is redirected by the sample into an emitted radiation distribution at least a portion of which is intercepted and reflected by the reflector;
   c) a detector for receiving the emitted radiation distribution reflected by the reflector;
   d) a source aperture disposed along the optical path between the source and the reflector;
   e) a beam steerer for moving the source aperture with respect to the reflector to direct the source radiation beam to the first location on the reflector; and
   f) a beam splitter disposed along the optical path between the source aperture and the reflector, for receiving the source radiation beam and directing the source radiation beam to the reflector.

105. The apparatus according to claim 104 wherein the emitted radiation distribution comprises at least one radiation ray and wherein the detector comprises an array of radiation detecting elements disposed along the detection plane, wherein the radiation ray strikes a respective radiation detecting element, the respective element associated with the angle of emission with which the radiation ray was emitted from the sample.

106. The apparatus according to claim 105 wherein detector comprises an orthographic lens having an aperture stop disposed proximate to the focal point of the lens.

107. An apparatus for measuring, as a function of incident beam geometry, the energy distribution emitted from a sample comprising:
 a) a source for producing a substantially collimated source radiation beam directed along an optical path;
 b) a paraboloidal reflector, having an optical axis disposed parallel to the optical path, positioned to intercept the collimated radiation beam at a first location on the reflector and to focus the intercepted beam to form an incident beam that strikes the sample at a selected sample location with a selected angle of incidence, whereupon the radiation from the incident beam is redirected by the sample into an emitted radiation distribution at least a portion of which is intercepted and reflected by the reflector;
 c) a detector for receiving the emitted radiation distribution reflected by the reflector; and
 d) a beam steerer comprising at least one rotatable aperture disk for directing the radiation beam to the first location on the reflector through the rotation of the disk.

108. The apparatus according to claim 107 wherein the aperture disk comprises multiple apertures.

109. The apparatus according to claim 107 wherein the beam steerer comprises a multi-aperture disk and a slit-aperture disk registered to the multi-aperture disk along a common axis of rotation.

110. The apparatus according to claim 109 wherein the apertures of multi-aperture disk are disposed in a spiral pattern.

* * * * *